(12) United States Patent
Marzouk et al.

(10) Patent No.: US 6,706,810 B2
(45) Date of Patent: Mar. 16, 2004

(54) PRIMER/PRIMER SURFACER

(75) Inventors: Mohsen S. Marzouk, Sharonville, OH (US); Jeffrey Andrew Reynolds, Cincinnati, OH (US)

(73) Assignee: Illinois Tool Works, Inc., Glenview, IL (US)

( * ) Notice: Subject to any disclaimer, the term of this patent is extended or adjusted under 35 U.S.C. 154(b) by 0 days.

(21) Appl. No.: 09/811,199

(22) Filed: Mar. 16, 2001

(65) Prior Publication Data

US 2002/0132916 A1 Sep. 19, 2002

(51) Int. Cl.$^7$ .................................................. C08K 3/00
(52) U.S. Cl. ........................................ 524/599; 502/160
(58) Field of Search ............................ 524/599; 502/160

(56) References Cited

U.S. PATENT DOCUMENTS

| | | | | |
|---|---|---|---|---|
| 3,865,617 A | * | 2/1975 | Shimizu | 117/113 |
| 3,867,461 A | * | 2/1975 | Leveskis | 260/610 |
| 4,107,230 A | | 8/1978 | Turnbo et al. | |
| 4,322,460 A | | 3/1982 | Howe et al. | |
| 4,904,749 A | * | 2/1990 | Brusky et al. | 526/201 |
| 5,236,975 A | * | 8/1993 | Sekine | 523/510 |
| 5,843,221 A | * | 12/1998 | Parish | 106/469 |
| 5,965,672 A | | 10/1999 | Agari et al. | |
| 5,993,116 A | | 11/1999 | Paxton et al. | |
| 6,051,242 A | * | 4/2000 | Patel et al. | 424/401 |

* cited by examiner

Primary Examiner—Edward J. Cain
(74) Attorney, Agent, or Firm—Dinsmore & Shohl LLP

(57) ABSTRACT

The present invention provides for a primer composition that will lower the VOC, maintain excellent performance of the primer, and improve the mix ratio. The primer composition contains a mixture of methyl ethyl ketone peroxide (MEKP) with a solvent. The solvent keeps the MEKP from decomposing while the potency to cure the prime is kept in the same required time.

10 Claims, No Drawings

PRIMER/PRIMER SURFACER

BACKGROUND OF THE INVENTION

The present invention relates to primers/primer surfacers, that will be applied to any substrate that will be painted and more particularly to metal, fiberglass, SMC, plastic or wood that will be painted, and it particularly relates to a primer/primer surfacer to be used in the field of automotive, marine, agricultural and industrial equipment.

There are many primer/primer surfacers on the market which used as primer to prepare the surface to be painted. Traditional primers are being gradually pushed out of the market due to changing environmental regulations. As a result, trying to create a new, volatile organic compound (VOC) compliant, high performance and user friendly primer has become important for manufacturers, such as manufacturers of automotive, marine, agricultural and industrial equipment.

Traditional urethane technology has thus far not been successfully used because of problems integrating high solids, and exempt (VOC compliant) solvent into urethane primers. Shrinkage and other poor performance characteristics have not been overcome. The epoxy system also suffers from poor performance characteristics, including long dry time and poor sanding. Acrylics (air-dry) systems have inherent VOC and shrinkage problem, and poor integrity.

The traditional polyester system brought solid performance at VOC complaint levels, with most of the benefits of epoxy and urethanes obtained without the liabilities of shrink, slow dry/cure, and poor sanding. The problem with traditional polyester primer technology is the catalyzation amount. The catalyzation amount was very subjective and prone to error. In addition, the ketone peroxide, such as methyl ethyl ketone-peroxide (MEKP), traditionally used as the catalyst has oxidative and corrosive properties that present some risks from a health and safety point of view. Also, the concentrated peroxide is susceptible to premature decomposition, gassing, and loss of reactive properties (active oxygen) if stored improperly.

There have been attempts to overcome these deficiencies by using vinyl polyester (VPE). Vinyl ester, polyester, and VPE are cured with MEKP at 2% by weight. One problem is to find a way to stabilize the MEKP so that it can be mixed with the primer in a ratio other than 2%.

Thus, there is a need in the art for a new polyester system that will lower the VOC, maintain the excellent performance of a primer, and improve the mix ratio.

SUMMARY OF THE INVENTION

This invention fulfills that need by providing a primer composition that will lower the VOC, maintain excellent performance of the primer, and improve the mix ratio. This is accomplished by mixing methyl ethyl ketone peroxide (MEKP) with a solvent which is either ethyl acetate, methyl acetate, t-butyl acetate, or mixtures thereof. The solvent keeps the MEKP from decomposing while keeping the potency to cure the primer in the same required time.

In accordance with one embodiment of the present invention, a primer composition is provided comprising an ester, methyl ethyl ketone peroxide, and a sufficient amount of solvent to stabilize the methyl ethyl ketone peroxide. The ester in primer composition is selected from the groups consisting of polyester, vinyl ester, vinyl polyester, and mixtures thereof. The solvent in the primer composition is mixed with the methyl ethyl ketone peroxide.

In accordance with another embodiment of the present invention, a method of stabilizing a primer composition is provided comprising the steps of mixing methyl ethyl ketone peroxide with a sufficient amount of solvent to stabilize the methyl ethyl ketone peroxide, then adding the mixture to a primer composition. The solvent used in the method of stabilizing a methyl ethyl ketone peroxide catalyst is selected from the group consisting of ethyl acetate, methyl acetate, t-butyl acetate, and mixtures thereof.

In accordance with another embodiment of the present invention, a stabilized methyl ethyl ketone peroxide catalyst is provided comprising methyl ethyl ketone peroxide and a sufficient amount of a solvent to stabilize the methyl ethyl ketone peroxide. The solvent in the stabilized methyl ethyl ketone peroxide catalyst is selected from the group consisting of ethyl acetate, methyl acetate, t-butyl acetate, and mixtures thereof.

DETAILED DESCRIPTION OF THE PREFERRED EMBODIMENTS

The present invention utilizes a stabilized MEKP in order to create a new polyester system that lowers the VOC, maintains the excellent performance of a primer, and improves the mix ratio. The stabilized MEKP is produced by adding a solvent to the MEKP. More specifically, by adding either ethyl acetate, methyl acetate, t-butyl acetate, or mixtures thereof to MEKP, the MEKP is more stable and provides a longer shelf life.

"The primer composition comprises an ester, a methyl ethyl ketone peroxide, and a sufficient amount of solvent to stabilize the methyl ethyl ketone peroxide. The ester can be polyester, vinyl ester, vinyl polyester, and mixtures thereof. The amount of the ester is in the range of 20–40% by weight. The amount of methyl ethyl ketone peroxide used is in the range of 1–5% by weight The amount of methyl ethyl ketone peroxide in the primer composition is 5–20% by weight."

The solvent in the primer composition is mixed with the methyl ethyl ketone peroxide to form a solution. The solution is then added to the primer, giving the primer a shelf life over 6 months. The solvent is selected from ethyl acetate, methyl acetate, t-butyl acetate, and mixtures thereof.

The method of stabilizing the primer composition comprises the step of mixing methyl ethyl ketone peroxide with a sufficient amount of solvent to stabilize the methyl ethyl ketone peroxide, then adding the mixture to the primer composition.

The stabilized methyl ethyl ketone peroxide catalyst comprises methyl ethyl ketone peroxide and a sufficient amount of a solvent to stabilize the methyl ethyl ketone peroxide. The amount of methyl ethyl ketone peroxide catalyst used is in the range of 15–40% by weight. The shelf life of the stabilized methyl ethyl ketone peroxide catalyst is over 6 months.

What is claimed is:

1. A primer composition comprising:
   an ester, and
   a stabilized methyl ethyl ketone peroxide catalyst consisting essentially of methyl ethyl ketone peroxide and a sufficient amount of solvent to stabilize the methyl ethyl ketone peroxide, wherein the solvent is selected from ethyl acetate, methyl acetate, t-butyl acetate, or mixtures thereof;
   wherein the primer composition has a shelf life of over 6 months.

2. The primer composition of claim 1 wherein the ester is selected from polyester, vinyl ester, vinyl polyester, or mixtures thereof.

3. The primer composition of claim 1 wherein the amount of the ester is between 20% and 40% by weight.

4. The primer composition of claim 1 wherein the amount of methyl ethyl ketone peroxide is between 1% and 5% by weight.

5. The primer composition of claim 1 wherein the amount of methyl ethyl ketone peroxide is between 5% and 20% by weight.

6. A method of making a stabilized primer composition comprising:

mixing methyl ethyl ketone peroxide with a sufficient amount of solvent to form a stabilized methyl ethyl ketone peroxide catalyst having a shelf life of over 6 months, wherein the solvent is selected from ethyl acetate, methyl acetate, t-butyl acetate, or mixtures thereof; and adding the stabilized methyl ethyl ketone peroxide catalyst to a primer composition to form the stabilized primer composition, wherein the stabilized primer composition has a shelf life of over 6 months.

7. The method of claim 6 wherein the amount of methyl ethyl ketone peroxide is between 1% and 5% by weight.

8. The method of claim 6 wherein the amount of methyl ethyl ketone peroxide is between 5% and 20% by weight.

9. A stabilized methyl ethyl ketone peroxide catalyst consisting essentially of:

methyl ethyl ketone peroxide; and a sufficient amount of a solvent to stabilize the methyl ethyl ketone peroxide to form the stabilized methyl ethyl ketone peroxide catalyst, the solvent selected from ethyl acetate, methyl acetate, t-butyl acetate, or mixtures thereof, wherein the stabilized methyl ethyl ketone peroxide catalyst has a shelf life of over 6 months.

10. The stabilized methyl ethyl ketone peroxide catalyst of claim 9 wherein the amount of methyl ethyl ketone peroxide is between 1% and 5% by weight.

* * * * *